United States Patent
Martin et al.

(10) Patent No.: US 11,311,417 B2
(45) Date of Patent: Apr. 26, 2022

(54) SINGLE-STAGE DOCKING OF A FEMTOSECOND LASER

(71) Applicant: Alcon Inc., Fribourg (CH)

(72) Inventors: Peter Martin, Velden (DE); Jörg Grampp, Vorra (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 15/744,675

(22) PCT Filed: Jan. 28, 2017

(86) PCT No.: PCT/IB2017/050463
§ 371 (c)(1),
(2) Date: Jan. 12, 2018

(87) PCT Pub. No.: WO2018/138552
PCT Pub. Date: Aug. 2, 2018

(65) Prior Publication Data
US 2019/0336341 A1    Nov. 7, 2019

(51) Int. Cl.
*A61F 9/008* (2006.01)
*A61F 9/009* (2006.01)
*A61N 5/06* (2006.01)

(52) U.S. Cl.
CPC .......... *A61F 9/00836* (2013.01); *A61F 9/009* (2013.01); *A61F 9/00804* (2013.01); *A61N 5/0613* (2013.01); *A61F 2009/00872* (2013.01)

(58) Field of Classification Search
CPC ................................ A61F 9/009; A61F 9/008
USPC ............................................................. 606/4
See application file for complete search history.

(56) References Cited

U.S. PATENT DOCUMENTS

| 6,142,630 A | 11/2000 | Koester |
| 8,858,581 B2* | 10/2014 | Robi ........................ A61F 9/009 606/166 |
| 2010/0228236 A1* | 9/2010 | Muhlhoff ............ A61F 9/00827 606/4 |
| 2012/0008377 A1 | 1/2012 | Chuang et al. |

(Continued)

FOREIGN PATENT DOCUMENTS

| EP | 1844745 A2 | 10/2007 |
| WO | 2006/128038 A2 | 11/2006 |

(Continued)

OTHER PUBLICATIONS

Office Action for Indian Patent Application No. 201917023719, dated Mar. 25, 2021, with English translation; 6 pages.

*Primary Examiner* — Jon Eric C Morales
(74) *Attorney, Agent, or Firm* — Baker Botts LLP

(57) ABSTRACT

The present disclosure provides a one-piece patient interface for single-stage docking of a femtosecond laser. The one-piece patient interface includes an upper circular portion, a lower conical portion integrally formed with the upper circular portion, an applanation plate in the lower conical portion, and a vacuum connection. The applanation plate may be at least partially coated with an applanation plate coating that is substantially transparent to treatment wavelengths of the femtosecond laser and substantially reflective to non-treatment wavelengths. The disclosure further provides a method for single-stage docking of a femtosecond laser and a system for cutting a flap on an eye using a femtosecond laser.

12 Claims, 3 Drawing Sheets

(56) References Cited

U.S. PATENT DOCUMENTS

2014/0104600 A1    4/2014  Rathjen
2017/0000647 A1*  1/2017  Schuele .............. A61F 9/00825

FOREIGN PATENT DOCUMENTS

WO      2008/150330 A1    12/2008
WO      2012/041347 A1    4/2012
WO      2013/053367 A1    4/2013

* cited by examiner

SINGLE-STAGE DOCKING OF A FEMTOSECOND LASER

TECHNICAL FIELD

The present disclosure relates to ophthalmic surgery and surgical equipment, and more specifically, to systems and methods for single-stage docking of a femtosecond laser for ophthalmic surgery.

BACKGROUND

In ophthalmology, ophthalmic surgery is performed on the eye and accessory visual structures to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make a tremendous difference in the patient's vision after the surgery.

One type of ophthalmic surgery, refractive eye surgery, is used to correct a variety of vision problems. One common such refractive surgery is known as LASIK (laser-assisted in situ keratomileusis) and is used to correct myopia and hyperopia, astigmatism, or more complex refractive errors. Other ophthalmic surgeries may correct corneal defects or other problems. For instance, phototherapeutic keratectomy (PTK) may be used to remove diseased corneal tissue or corneal irregularities either alone or in combination with LASIK. Another common ophthalmic surgery is the removal of cataracts.

During LASIK, PTK, cataract surgery, and other ophthalmic surgeries, corrective procedures are commonly performed on interior parts of the eye, such as the corneal stroma or the lens, rather than on the eye surface. This practice tends to improve surgical outcomes by allowing the corrective procedure to be targeted to the most effective part of the eye, by keeping the outer, protective parts of the cornea largely intact, and for other reasons.

The interior part of the eye may be accessed in a variety of manners, but frequently access involves cutting a flap in the cornea or otherwise cutting the cornea. Corneal cutting is often performed by a femtosecond laser that creates focused ultrashort pulses, eliminating collateral damage of surrounding tissues associated with slower lasers and complications associated with mechanical cutting instruments, such as blades. Femtosecond lasers can therefore be used to dissect tissue on a microscopic level.

Femtosecond laser ophthalmic surgery typically includes docking, imaging, analysis, and treatment. Docking is typically a two-stage procedure, in which a suction ring is first placed on the eye and a suction cone is then lowered toward the patient's eye and docked to the suction ring. The suction ring is often held in place and in contact with the eye by vacuum suction that is turned on after the suction ring is properly positioned on the eye. When the suction cone is properly docked to the suction ring, a second vacuum may be turned on to hold the suction cone in place and in contact with the suction ring. The pressure on the patient's eye from the docked suction cone flattens the patient's cornea (known as applanation) and holds it in position for treatment. A curved cone, which does not flatten the cornea, may also be used for the docking procedure.

SUMMARY

The present disclosure provides one-piece patient interface for single-stage docking of a femtosecond laser, the one-piece patient interface comprising an upper circular portion, a lower conical portion integrally formed with the upper circular portion, an applanation plate in the lower conical portion, and a vacuum connection.

In additional embodiments, which may be combined with one another unless clearly exclusive: the applanation plate comprises an applanation plate coating that is substantially transparent to treatment wavelengths of a femtosecond laser and substantially reflective to non-treatment wavelengths; the treatment wavelengths of the femtosecond laser are near-infrared wavelengths greater than 900 nm and the non-treatment wavelengths include ultraviolet wavelengths in the range of 200-400 nm; the treatment wavelengths of the femtosecond laser are near-infrared wavelengths greater than 900 nm and the non-treatment wavelengths include ultraviolet wavelengths in the range of 200-400 nm and visible wavelengths in the range of 400-700 nm; the applanation plate coating is coated on an exterior side of the applanation plate; the applanation plate coating is biocompatible, biologically inactive, does not irritate an eye when in contact, and does not leave residue on the eye when in contact; and the applanation plate coating is coated on an interior side of the applanation plate.

The present disclosure further provides a method for single-stage docking of a femtosecond laser comprising connecting a vacuum to a vacuum connection of a one-piece patient interface, the patient interface comprising an upper circular portion, a lower conical portion integrally formed with the upper circular portion, an applanation plate in the lower conical portion, and the vacuum connection, connecting a femtosecond laser to the one-piece patient interface, positioning the one-piece patient interface on an eye, and activating the vacuum to hold the patient interface in contact with the eye and to applanate the eye.

In additional embodiments, which may be combined with one another unless clearly exclusive: the method further comprises connecting or activating no additional vacuum.

The present disclosure further provides a system for cutting a flap on an eye using a femtosecond laser, the system comprising a femtosecond laser operable to supply a treatment wavelength, a control device operable to adjust a position of the femtosecond laser, and a one-piece patient interface. The one-piece patient interface includes an upper circular portion, a lower conical portion integrally formed with the upper circular portion, an applanation plate in the lower conical portion, the applanation plate coated with an applanation plate coating that is substantially transparent to treatment wavelengths of a femtosecond laser and substantially reflective to non-treatment wavelengths, and a vacuum connection. The system further includes a detection device operable to detect reflected non-treatment wavelengths and generate data relating to the reflected non-treatment wavelengths detected, and a processor operable to receive data from the detection device relating to the reflected non-treatment wavelengths detected, and generate measurements for cutting a flap using treatment wavelengths of the femtosecond laser.

In additional embodiments, which may be combined with one another unless clearly exclusive: the treatment wavelengths of the femtosecond laser are near-infrared wavelengths greater than 900 nm and the non-treatment wavelengths include ultraviolet wavelengths in the range of 200-400 nm; the treatment wavelengths of the femtosecond laser are near-infrared wavelengths greater than 900 nm and the non-treatment wavelengths include ultraviolet wavelengths in the range of 200-400 nm and visible wavelengths in the range of 400-700 nm; the applanation plate coating is coated on an exterior side of the applanation plate; the applanation plate coating is biocompatible, biologically inactive, does not irritate an eye when in contact, and does not leave residue on the eye when in contact; and the applanation plate coating is coated on an interior side of the applanation plate.

The above apparatus may be used with the above method and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

The present disclosure provides an apparatus and method for single-stage docking of a femtosecond laser for ophthalmic surgery. As used herein, single-stage refers to a single centering and alignment process prior to applanating the eye. The docking apparatus includes a one-piece patient interface that has an upper circular portion and a lower conical portion integrally formed with the upper circular portion. The upper circular portion may be connected to a femtosecond laser. The lower conical portion has an applanation plate that may applanate the cornea of the eye. The applanation plate may have an applanation plate coating that is substantially transparent to the wavelengths of the femtosecond laser that cut a flap in the cornea of the eye (the "treatment wavelengths"), but is substantially reflective to other wavelengths of the femtosecond laser (the "non-treatment wavelengths"). For example, "substantially transparent" may mean allowing at least 90% of radiation at the treatment wavelengths to pass if the coating is transparent, and "substantially reflective" may mean reflecting at least 80% of radiation at the non-treatment wavelengths if the coating is reflective. The applanation plate coating may allow for accurate measurement of the length of the one-piece patient interface because it provides a surface reflective to non-treatment wavelengths, even when positioned on an eye. The method includes connecting a vacuum to a one-piece patient interface, connecting a femtosecond laser to the one-piece patient interface, positioning the one-piece patient interface on an eye, and activating the vacuum to hold the patient interface in contact with and to applanate the eye.

The present disclosure also provides a system for cutting a flap on an eye using a femtosecond laser. The system includes a femtosecond laser, a control device to adjust a position of the femtosecond laser, a one-piece patient interface, a detection device that can detect reflected non-treatment wavelengths and generate data relating to the reflected non-treatment wavelengths detected, and a processor that can receive data from the detection device relating to the reflected non-treatment wavelengths detected and generate measurements for cutting a flap.

Figure 1:
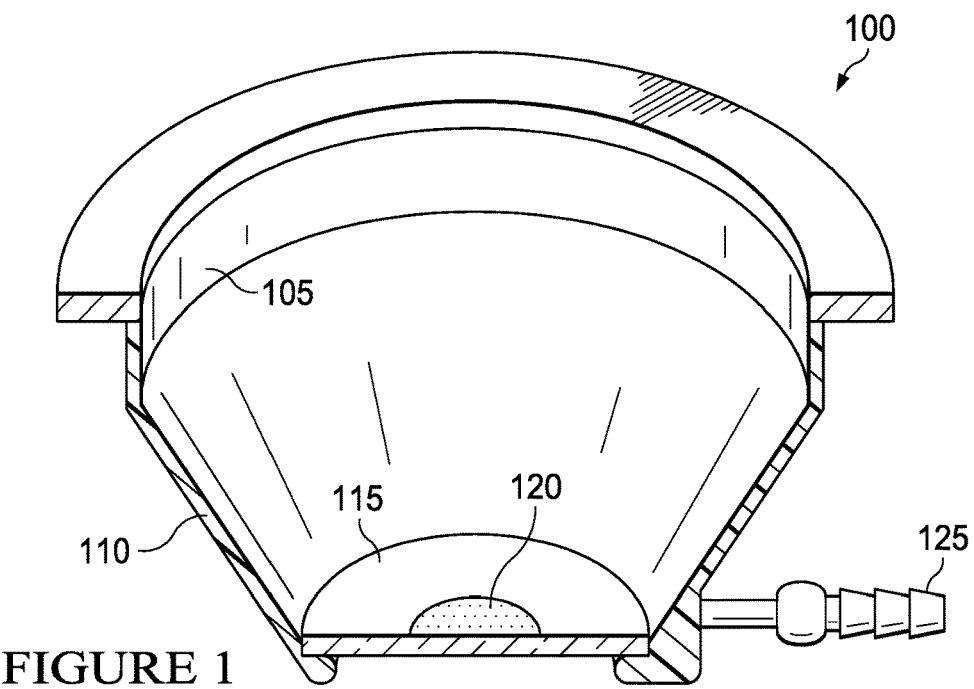
FIG. 1 is a schematic representation of an apparatus for single-stage docking of a femtosecond laser.

This disclosure relates to single-stage docking of a femtosecond laser, which, in contrast to prior two-stage docking procedures, may allow the user to take optical measurements more readily, perform docking faster, and begin treatment sooner. In single-stage docking, only the one-piece patient interface described in FIG. 1 is centered and aligned on the eye. The femtosecond laser is connected directly to the one-piece patient interface, which is then positioned on an eye.

In contrast, two-stage docking involves first properly positioning a suction ring on an eye, activating a first vacuum, lowering and centering a suction cone on the suction ring, and activating a second vacuum. The first vacuum holds the suction ring in place and in contact with the eye; the second vacuum holds the suction cone in place and in contact with the suction ring and the eye, applanating the cornea of the eye. Accordingly, two-stage docking refers to two centering and alignment steps required to get the femtosecond laser in a position appropriate for treatment, the first for the suction ring and the second for the suction cone. A two-stage docking procedure takes more time to complete and has a greater likelihood of error because multiple components (the suction ring and the suction cone) must all be centered in relation to each other and in relation to a user-selected centering axis. Further, a two-stage docking procedure requires two vacuums or vacuum connections because the suction ring must be held in place and in contact with the eye independent from the suction cone. Use of multiple vacuums or vacuum connections increases the likelihood of inconsistent suction, which may result in too great of a suction force exerted upon the eye or too little suction to applanate the eye and hold the docking components in place.

In contrast, a one-piece patient interface as disclosed herein removes the need for two vacuums because the one-piece patient interface may be held in contact with the eye using only one vacuum. However, although described herein in connection with only one vacuum, multiple vacuums or vacuum connections may be used with the one-piece patient interface to hold it in contact with the eye in the proper position. Because they can operate with one vacuum or one vacuum connection, the apparatus, systems and methods disclosed may decrease error resulting from inconsistent suction on the eye or equipment failure associated with multiple vacuums or vacuum connections.

To take measurements for a surgical procedure involving two-stage docking, the user typically positions the suction cone on the eye in what is often called the preliminary latching position. This step is often called the focus check. Because the suction cone applanates the eye, the user may then take any measurements necessary to cut a flap or perform any subsequent surgical procedure. Next, the suction cone is removed from the eye and the measurements taken may be used to program the femtosecond laser to cut the flap. To dock the eye for cutting the flap, the user will properly position the suction ring on the eye, turn on the first vacuum, center the suction cone in relation to the properly positioned suction ring, and turn on the second vacuum. When the eye is properly docked, it is referred to as being in treatment position. Because the measurements are taken in preliminary latching position, the user generally assumes that the measurements taken are still applicable to and accurate for the treatment position as well, but this may not be the case. Although such measurements are taken and actions are performed carefully, user error still pervades.

In contrast, a one-piece patient interface as described herein may improve measurement accuracy and improve treatment because it may remain in place after measurements are taken and because of improvements in its design.

A one-piece patient interface has an applanation plate, which applanates the eye, built into its lower conical portion. This applanation plate may have an applanation plate coating that is substantially transparent to treatment wavelengths of the femtosecond laser and substantially reflective to non-treatment wavelengths of the femtosecond laser. The applanation plate coating is useful because the reflection of the femtosecond laser beam is very low and is not optimal for accurate measurements. In particular, when tests were performed on two-stage docking systems, birefringence occurred, interfering with measurement accuracy.

Thus, by detecting reflected non-treatment wavelengths of the applanation plate coating, the user may take measurements of the eye via detection and analysis of these reflected non-treatment wavelengths while the eye is docked and applanated. Such measurements may be used to cut a flap, for example, without undocking the one-piece interface from the eye (unless measurements indicate that repositioning is needed). Measurements need not be taken in a preliminary latching position, which may increase the accuracy and relevance of measurements taken. In addition, because the patient must remain as still as possible during flap cutting and treatment, any decease in docking and treatment duration, such as may result from single-stage docking, is a significant benefit to the patient and decreases risks associated with unintentional movements. Generally, two-stage docking may take a user at least a few seconds to position the suction ring on the eye and may take an additional 5-30 seconds to dock the suction cone an femtosecond laser, although docking in 5 seconds is uncommon and often only achieved by experienced users. In contrast, single-stage docking may only take a reasonably experienced user 5 seconds to dock the one-piece patient interface once attached to the femtosecond laser, and may decrease the amount of time for docking in half for inexperienced users.

Further, in two-stage docking, mechanical deformation of the suction cone may occur, for example, when the suction cone is lowered too far in the z-direction (as defined further below), manually or via a control device. Any such mechanical deformations affect focus control and the measurements taken in the preliminary latching position. By allowing the user to connect the femtosecond laser directly, the one-piece patient interface as disclosed herein minimizes or eliminates the risk of such inadvertent mechanical deformations and resulting errors in eye measurements.

Figure 2:
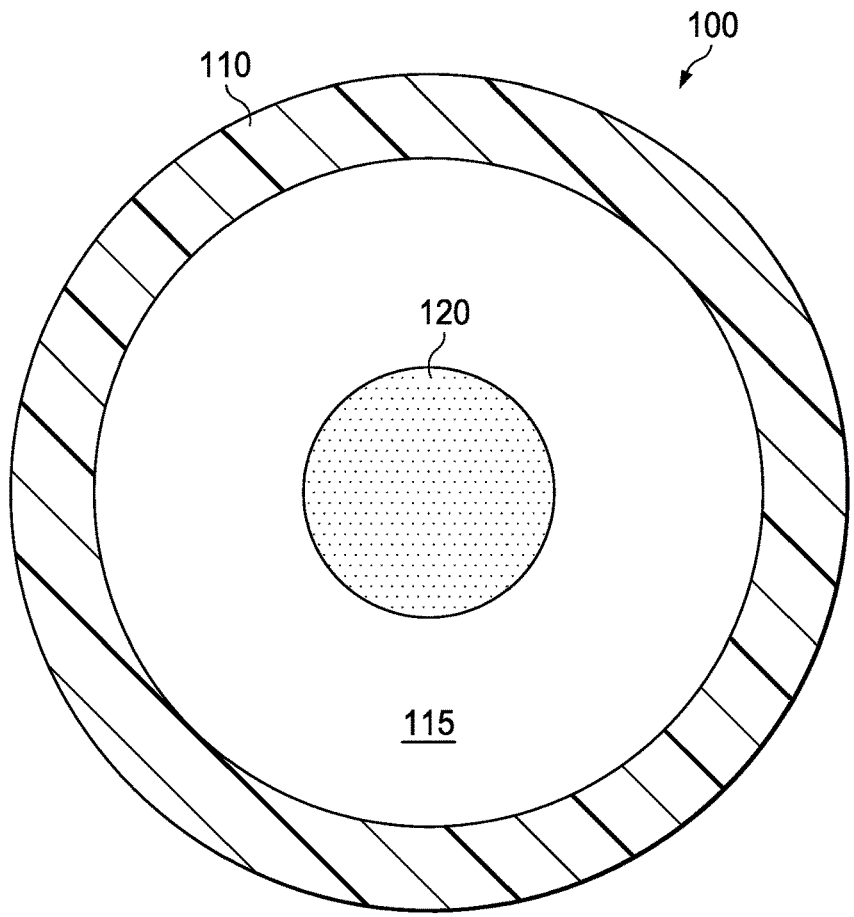
FIG. 2 is a schematic top-view representation of an applanation plate with an applanation plate coating.

Referring now to FIG. 1 and FIG. 2, one-piece patient interface 100 has an upper circular portion 105 and a lower conical portion 110, and vacuum connection 125, which may be a tubular member extending from one-piece patient interface 100. Vacuum connection 125 may be connected to lower conical portion 110 in a manner similar to that found in conventional suction rings. In particular, it may connect with an inner open area defined by lower conical portion 110 so that the vacuum may be applied to an eye to hold one-piece patient interface 100 in place on the eye.

Lower conical portion 110 has an applanation plate 115. Applanation plate 115 has an applanation plate coating 120 (a top view of which is shown in FIG. 2). Applanation plate 115 may be, for example, a sterile glass applanation plate. Applanation plate coating 120 is substantially transparent to treatment wavelengths of the femtosecond laser, but is substantially reflective for non-treatment wavelengths of the femtosecond laser. Applanation plate coating 120 may be, for example, a biocompatible polymer that is substantially transparent to the femtosecond laser's treatment wavelengths and substantially reflective of non-treatment wavelengths.

Applanation plate coating 120 may be substantially transparent to the treatment wavelengths of the femtosecond laser and substantially reflective to non-treatment wavelengths. As shown, applanation plate coating 120 is only coated on the exterior side of applanation plate 115, which is the side facing the eye during use. In FIG. 1 and FIG. 2, applanation plate coating 120 is only partially coated on the surface of the exterior side in a circular shape near the center of the applanation plate. In other variations, the applanation plate coating may be coated on the entirety or on any part of one or both sides of the applanation plate. The applanation plate coating may be applied to either side of the applanation plate, for instance, the exterior side of the applanation plate that faces the eye during use or the interior side of the applanation plate that does not face the eye during use. Alternatively, the applanation plate coating may be coated on both sides of the applanation plate (the exterior side and the interior side). Often, only the exterior side of the applanation plate may be coated due to manufacturing concerns or because this may present less interference with the optics of the femtosecond laser. The applanation plate may be coated with standard coatings customized to be substantially transparent to treatment wavelengths, but substantially reflective to non-treatment wavelengths. The applanation plate coating may be of any diameter suitable for the applanation plate used, for example, the applanation plate coating may be 12 mm in diameter.

Applanation plate coating 120 or any other applanation plate coating may be biocompatible and biologically inactive so that it does not irritate the eye upon contact. The applanation plate coating may also not leave residue on the eye after contact. Such an applanation plate coating may be more beneficial when on the exterior side of the applanation plate.

Generally, treatment wavelengths of the femtosecond laser are near-infrared and greater than 900 nm, or infrared and greater than 1000 nm, often approximately 1030 nm or 1053 nm. Non-treatment wavelengths include, for example, ultraviolet wavelengths, which are in the range of 200-400 nm, and visible wavelengths, which are in the range of 400-700 nm. Thus the applanation plate coating may, for example, be transparent to treatment wavelengths of the femtosecond laser that are infrared wavelengths greater than 900 nm or greater than 1000 nm, and reflective to the non-treatment wavelengths that are ultraviolet wavelengths in the range of 200-400 nm and visible wavelengths in the range of 400-700 nm. In another example, the applanation plate coating may be transparent to treatment wavelengths of the femtosecond laser that are infrared wavelengths greater than 1000 nm, and reflective to the non-treatment wavelengths that are ultraviolet wavelengths in the range of 200-400 nm.

Due to the reflectivity of the applanation plate coating to certain wavelengths, the one-piece patient interface may allow the user to take optical measurements when the one-piece patient interface is in treatment position. The user may take measurements of the eye via detection and analysis of reflected non-treatment wavelengths and may then begin treatment of the eye without removing and redocking the one-piece patient interface.

Figure 3:
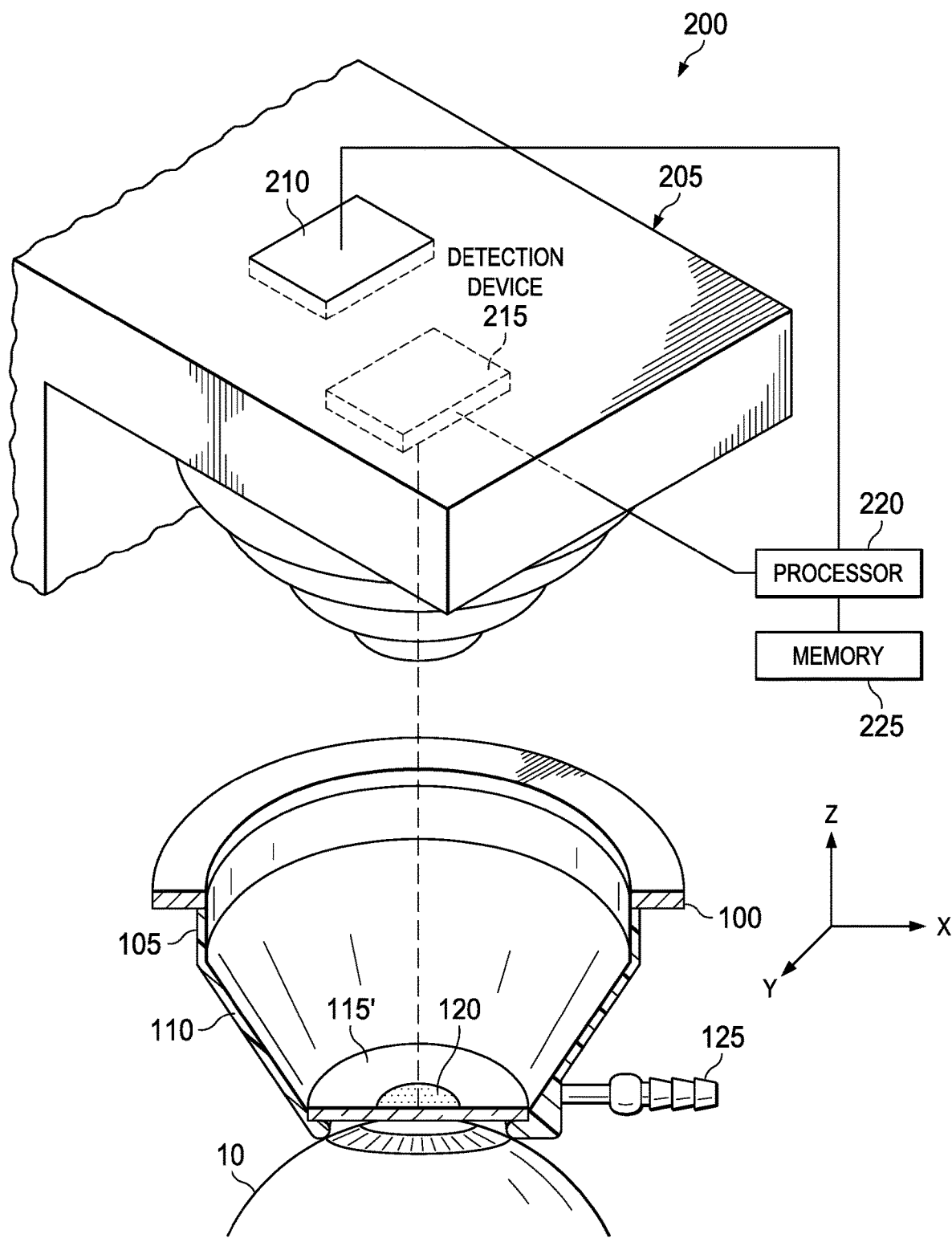
FIG. 3 is a schematic representation of a system for cutting a flap on an eye using a femtosecond laser.

FIG. 3 is a schematic representation of a system 200 for cutting a flap on an eye using a femtosecond laser 205. As shown, system 200 includes a femtosecond laser 205, with control device 210, which can adjust a position of the femtosecond laser in the x, y, or z-directions. The x and y-directions may be defined in the plane roughly perpendicular to the apex of the cornea and the z-direction may be defined as the plane roughly perpendicular to that of the x and y-directions. Femtosecond laser 205 is also connected to processor 220 and memory 225. System 200 also includes one-piece patient interface 100, which has an upper circular portion 105 and a lower conical portion 110, and vacuum connection 125. Lower conical portion 110 has an applanation plate 115, with applanation plate coating 120. As shown in FIG. 3, applanation plate 115 is in contact with eye 10 and is applanating eye 10.

Femtosecond laser 205 may be further connected to detection device 215 that detects non-treatment wavelengths reflected by applanation plate coating 120 and generates data that may be transmitted to processor 220, processed, and used to generate measurements that may then be used for cutting a flap in eye 10 using femtosecond laser 210. For example, detection device 215 may include standard photodiodes sensitive for the non-treatment wavelengths or may be a digital camera connected to processor 220.

Data generated by detection device 210 and measurements generated by processor 220 may be compared to a surgical plan to determine if surgery may proceed, evaluated to determine if the one-piece patient interface 100 or femtosecond laser 210 is positioned correctly, to program femtosecond laser 210 to cut a flap in the cornea of eye 10, or otherwise used in connection with cutting a flap in the cornea of eye 10 using femtosecond laser 210.

Figure 4:
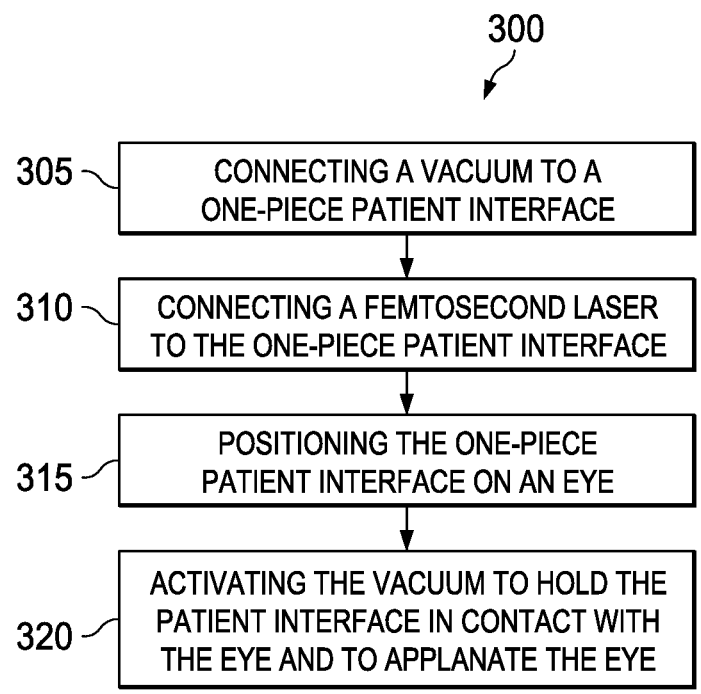
FIG. 4 is a flow chart of a method for single-stage docking of a femtosecond laser.

FIG. 4 is a flow chart of a method 300 for single-stage docking of a femtosecond laser. The method may be used in connection with a docking apparatus and system as described herein, such as those described in FIGS. 1-3 above.

At step 305, a vacuum is connected to a one-piece patient interface, for example by connecting a tube from the vacuum to a vacuum connection on the patient interface. At step 310, a femtosecond laser is connected to the one-piece patient interface. The femtosecond laser may be connected so that it is in position to cut a flap in the cornea in of the eye.

At step 315, the one-piece patient interface is positioned on an eye. When positioned, the one-piece patient interface may centered in relation to a user-selected centering axis. This user-selected centering axis may be, for example, the center of the eye, the center of the pupil, or the visual axis of the patient. Depending on the patient, the visual axis may not pass through the absolute center of the patient's eye. At step 320, the vacuum is activated to hold the one-piece patient interface in contact with the eye and to applanate the eye.

The above disclosed subject matter is to be considered illustrative, and not restrictive, and the appended claims are intended to cover all such modifications, enhancements, and other embodiments which fall within the true spirit and scope of the present disclosure. For instance, variations of the present disclosure may use a curved cone that does not applanate the eye. To the maximum extent allowed by law, the scope of the present disclosure is to be determined by the broadest permissible interpretation of the following claims and their equivalents, and shall not be restricted or limited by the foregoing detailed description.

The invention claimed is:

1. A one-piece patient interface for single-stage docking of a femtosecond laser, the one-piece patient interface comprising:
    an upper circular portion;
    a lower conical portion integrally formed with the upper circular portion;
    an applanation plate in the lower conical portion, the applanation plate including an applanation plate coating that is substantially transparent to treatment wavelengths of a femtosecond laser and substantially reflective to non-treatment wavelengths, wherein the treatment wavelengths are near-infrared wavelengths greater than 900 nanometers (nm) and the non-treatment wavelengths are ultraviolet wavelengths between 200 and 400 nm; and
    a vacuum connection.

2. The one-piece patient interface of claim 1, wherein the non-treatment wavelengths further include visible wavelengths in the range of 400-700 nm.

3. The one-piece patient interface of claim 1, wherein the applanation plate coating is coated on an exterior side of the applanation plate.

4. The one-piece patient interface of claim 3, wherein the applanation plate coating is biocompatible, biologically inactive, does not irritate an eye when in contact, and does not leave residue on the eye when in contact.

5. The one-piece patient interface of claim 1, wherein the applanation plate coating is coated on an interior side of the applanation plate.

6. A method for single-stage docking of a femtosecond laser comprising:
    connecting a vacuum to a vacuum connection of a one-piece patient interface, the one-piece patient interface comprising:
        an upper circular portion;
        a lower conical portion integrally formed with the upper circular portion;
        an applanation plate in the lower conical portion, the applanation plate including an applanation plate coating that is substantially transparent to treatment wavelengths of a femtosecond laser and substantially reflective to non-treatment wavelengths, wherein the treatment wavelengths are near-infrared wavelengths greater than 900 nanometers (nm) and the non-treatment wavelengths are ultraviolet wavelengths between 200 and 400 nm; and
        the vacuum connection;
    connecting the femtosecond laser to the one-piece patient interface;
    positioning the one-piece patient interface on an eye; and
    activating the vacuum to hold the one-piece patient interface in contact with the eye and to applanate the eye.

7. The method of claim 6, further comprising connection or activating no additional vacuum.

8. A system for cutting a flap on an eye using a femtosecond laser, the system comprising:
    a femtosecond laser operable to supply a treatment wavelength;
    a control device operable to adjust a position of the femtosecond laser;
    a one-piece patient interface on an eye, the one-piece patient interface comprising:
        an upper circular portion;

a lower conical portion integrally formed with the upper circular portion;

an applanation plate in the lower conical portion, the applanation plate coated with an applanation plate coating that is substantially transparent to treatment wavelengths of the femtosecond laser and substantially reflective to non-treatment wavelengths, wherein the treatment wavelengths are near-infrared wavelengths greater than 900 nanometers (nm) and the non-treatment wavelengths are ultraviolet wavelengths between 200 and 400 nm; and a vacuum connection;

a detection device operable to detect reflected non-treatment wavelengths and generate data relating to the reflected non-treatment wavelengths detected; and a processor operable to:

receive data from the detection device relating to the reflected non-treatment wavelengths detected; and generate measurements for cutting a flap using treatment wavelengths of the femtosecond laser.

9. The system of claim 8, wherein the non-treatment wavelengths further include visible wavelengths in the range of 400-700 nm.

10. The system of claim 8, wherein the applanation plate coating is coated on an exterior side of the applanation plate.

11. The system of claim 8, wherein the applanation plate coating is biocompatible, biologically inactive, does not irritate an eye when in contact, and does not leave residue on the eye when in contact.

12. The system of claim 8, wherein the applanation plate coating is coated on an interior side of the applanation plate.

* * * * *